United States Patent
Kurukchi et al.

(10) Patent No.: US 10,399,914 B2
(45) Date of Patent: Sep. 3, 2019

(54) GREEN OIL REMOVAL FROM ETHYLENE PLANTS

(71) Applicant: Janus Technology Solutions, LLC, The Woodlands, TX (US)

(72) Inventors: Sabah A. Kurukchi, Houston, TX (US); Joseph M. Gondolfe, Magnolia, TX (US)

(73) Assignee: Janus Technology Solutions, LLC, The Woodlands, TX (US)

( * ) Notice: Subject to any disclaimer, the term of this patent is extended or adjusted under 35 U.S.C. 154(b) by 0 days.

(21) Appl. No.: 16/053,348

(22) Filed: Aug. 2, 2018

(65) Prior Publication Data

US 2019/0039974 A1 Feb. 7, 2019

Related U.S. Application Data

(60) Provisional application No. 62/541,001, filed on Aug. 3, 2017.

(51) Int. Cl.

| | |
|---|---|
| *C07C 7/04* | (2006.01) |
| *C07C 7/00* | (2006.01) |
| *C07C 7/167* | (2006.01) |
| *C07C 4/04* | (2006.01) |
| *C07C 7/11* | (2006.01) |
| *C10G 45/32* | (2006.01) |
| *C10G 69/06* | (2006.01) |
| *C10G 9/36* | (2006.01) |

(52) U.S. Cl.
CPC ............... *C07C 7/005* (2013.01); *C07C 4/04* (2013.01); *C07C 7/04* (2013.01); *C07C 7/11* (2013.01); *C07C 7/167* (2013.01); *C10G 9/36* (2013.01); *C10G 45/32* (2013.01); *C10G 69/06* (2013.01)

(58) Field of Classification Search
CPC .... C10G 45/40; C10G 11/22; C10G 2400/20; C10G 45/00; C10G 45/34; C07C 4/025; C07C 11/02
See application file for complete search history.

(56) References Cited

U.S. PATENT DOCUMENTS

2010/0217059 A1* 8/2010 Reyneke ................. C07C 4/025 585/651

OTHER PUBLICATIONS

"Back End C2 Hydrogenation for Ethylene Production." Kurukchi et al. dated Jan. 2007.

* cited by examiner

*Primary Examiner* — Sharon Pregler
(74) *Attorney, Agent, or Firm* — C. Tumey Law Group PLLC

(57) ABSTRACT

A method may comprise: feeding a backend deethanizer overhead stream comprising ethylene, ethane, and acetylene to a hydrogenation reactor; hydrogenating at least a portion of the acetylene in the backend deethanizer overhead stream to form a reactor effluent stream comprising ethylene, ethane, and green oil; feeding the reactor effluent stream to a gas/liquid coalescer; and removing at least a portion of the green oil from the reactor effluent stream to produce a cleaned effluent stream.

12 Claims, 5 Drawing Sheets

GREEN OIL REMOVAL FROM ETHYLENE PLANTS

BACKGROUND

Ethylene is one of the most dominant base petrochemicals, with a global production rate of approximately 180 million metric tons per annum production. Over sixty percent is used in the production of polyethylene with different properties such as high density polyethylene (HDPE), low density polyethylene (LDPE), and linear low-density polyethylene (LLDPE). Ethylene may be produced by steam cracking of hydrocarbons, predominantly saturated hydrocarbons. In steam cracking, gaseous feedstocks such as ethane, ethane and propane, and/or a mixture of propane and butane in the form of a liquefied petroleum gas (LPG), may be fed to a cracking furnace. Cracking furnaces operating on gaseous hydrocarbon feedstocks may be referred to as a gas cracker and cracking furnaces operating on liquid hydrocarbon feedstocks such as naphthas, and/or gas oils, may be referred to as liquid crackers. In general, the hydrocarbon feedstock to the steam cracker may be diluted with steam and thereafter briefly be exposed to a high temperature environment within a cracking furnace to produce a product gas comprising ethylene. Typically, the reaction temperature is relatively high, at approximately 850° C., but the reaction is only preferred to take place with minimal residence time. After the cracking temperature has been reached, the product gas may be quickly quenched to stop the reaction, for example, by quenching the product gas in a transfer line heat exchanger.

The product gas produced in the steam cracker may depend on the composition of the feedstock, the steam-to-hydrocarbon weight ratio, cracking temperature, and reaction residence time. Light hydrocarbon feeds such as ethane, LPG, or light naphtha may result in cracked product streams rich in lower olefins such as ethylene, propylene, and mixed butylenes. Liquid hydrocarbon feeds may yield the same lower olefins but additionally may produce aromatic-rich hydrocarbons and hydrocarbons which may be suitable for inclusion in gasoline or fuel oil.

A higher cracking temperature, also referred to as severity, may favor the production of ethylene and benzene, whereas lower severity may produce higher amounts of propylene, mixed butylenes and liquid products. The thermal process within the cracking furnaces may also result in the gradual deposition of coke on the inner walls of the radiant coils. The deposition may degrade the efficiency of the cracking furnaces, so design features of the radiant coils have evolved to minimize coke formation. Nonetheless, a cracking furnace can usually only maintain operation for a few months at a time between de-coke cycles. Decoking requires the furnace to be isolated from the process and then a flow of steam followed by a steam/air mixture followed by air-only through the radiant coils. This converts the hard solid carbon layer to carbon monoxide and carbon dioxide. Once this reaction is complete, the cracking furnace can be returned to service.

Steam crackers may be designed and built to favor ethylene production. As previously discussed, other byproducts may also be produced from steam cracking. For example, the co-production of these byproducts such as propylene, butanes and butenes, and aromatic pyrolysis gasoline may be dependent on the steam cracker design and feed composition, as illustrated in Table 1. Table 1 illustrates an example byproduct composition based on production of 100 tons of ethylene for different feedstocks. AGO is atmospheric gas oil.

TABLE 1

| | | Feedstock | | | | |
|---|---|---|---|---|---|---|
| | | Ethane | Propane | n-C4/i-C4 | Naphtha | AGO |
| Product | H2 + CO | 7.74 | 4.29 | 3.88 | 3.32 | 2.86 |
| | CH4 | 7 | 58.94 | 68.53 | 49.48 | 43.02 |
| | C2H2 | 0.95 | 1.69 | 1.58 | 2.22 | 1.37 |
| | C2H4 | 100 | 100 | 100 | 100 | 100 |
| | C2H6 | 66.27 | 11.53 | 11.56 | 11.03 | 11.07 |
| | C3H6 | 2.19 | 33.49 | 62.54 | 52.26 | 57.46 |
| | C3H8 | 0.23 | 18.71 | 2.17 | 1.23 | 1.25 |
| | C4's | 4.27 | 10.16 | 40.64 | 30.75 | 38.67 |
| | Pyrolysis Gasoline | 1.66 | 10.77 | 20.2 | 62.31 | 82.9 |
| | Pyrolysis Fuel Oil | 0.31 | 2.8 | 3.97 | 9.7 | 63.5 |

As one of ordinary skill in the art will appreciate, byproduct yields are also affected by the design of the cracking furnace and the severity of cracking. Acetylene is a byproduct of steam cracking. The yield of acetylene may be about 0.95 to about 2.22 tons per 100 tons of ethylene, depending on the feedstock and cracking severity. Light naphtha is typically cracked at the highest severity and may produce the most acetylene. Conversely, gas oils may be cracked at a relatively lower severity to reduce the rate of coking in the radiant coils. Consequently, the production of acetylene from atmospheric gas oils may be relatively lower than alternate feedstocks as shown in Table 1. There may be a significant range acetylene produced from a given steam cracker as feedstocks are varied. In general, the acetylene content of a marketable ethylene product must be lower than about 1 parts per million by weight (ppm). Acetylene removal is a critical step in the manufacture of ethylene, since failure to satisfy the acetylene content in the final ethylene specification may result in an unsaleable product.

Many different techniques are utilized in the removal of acetylene in the purification of product ethylene. This technology has progressed through distinct stages and encompasses various methods.

A method of acetylene removal may be solvent extraction. In the solvent extraction method, the acetylene is selectively absorbed into a solvent, such as n,n-dimethyl formamide (DMF), followed by its purification resulting in a merchantable acetylene product.

Another method of acetylene removal may be selective acetylene hydrogenation. The reactions that can occur in over the catalyst bed in acetylene hydrogenation units are listed below. An acetylene hydrogenation chemistry map is illustrated in FIG. 1.

$C_2H_2 + H_2 \rightarrow C_2H_4$ (desirable, causes ethylene gain)

$C_2H_4 + H_2 \rightarrow C_2H_6$ (undesirable)

$2C_2H_2 + H_2 \rightarrow C_4H_6$ (undesirable)

$C_4H_6 + H_2 \rightarrow C_4H_8$ (undesirable)

$nC_2H_2 + nH_2 \rightarrow$ Green Oil (undesirable oligomer, causes fouling)

Green oil formation and fouling may be a major issue in back-end hydrogenation reactors. The acetylene hydrogenation reactor may be placed at various different locations in the ethylene plant process flowsheet. For example, the hydrogenation reactor may treat a raw gas stream wherein the reactor may be placed downstream of a caustic tower. Another example may be a front-end selective catalytic hydrogenation reactor placed upstream of a demethanizer (DC1) treating either a front-end deethanizer (DC2) overhead stream, or a front-end depropanizer (DC3) overhead stream. Another example may be back-end catalytic hydrogenation reactors placed downstream of the DC1 treating the DC2 overhead stream. Some suitable catalysts may include, without limitation, nickel based catalyst for raw gas acetylene hydrogenation reactors, and palladium and/or bimetallic palladium/silver catalysts for front-end and back-end acetylene hydrogenation reactors.

For a raw cracked gas selective hydrogenation application, the reactor may be placed within the process gas compressor circuit, downstream of the caustic tower, but upstream of the main driers. Hence, the feed to this acetylene hydrogenation unit may be wet C4's and lighter, containing some C5's. Historically, this unit has been designed for operation with sulfided Ni/Co/Cr catalysts. Such acetylene hydrogenation units have been installed in many gas (ethane-only) crackers designed and built in the 1960's/early 70's and some remain in operation today. This operation may result in hydrogenation of C4 acetylenes and butadiene, hence minimizing the potential for fouling the bottoms section of downstream DC2 and/or DC3. Additionally, it may convert the majority of C3 and C4 acetylenes and diolefins into olefins, making the final C3 and C4 streams more attractive for fuel gas, and/or for recycle cracking. In such a process, the catalyst deactivation may be relatively rapid, especially for the first bed. This is primarily due to the presence of C4 and C5+ acetylenic and diolefinic species. Hence, a spare reactor system is needed for continuous operation of 5+ years. Typically, this hydrogenation unit operates with a net ethylene loss.

For a front-end DC2 and front-end DC3 selective hydrogenation process, the acetylene reactors may precede the DC1 in the process flow scheme. As a result, these reactor feeds contain a large excess of hydrogen, typically 10 to 35 mol percent. In a front-end DC2 configuration, the DC2 is the first distillation column and the reactors are on the overhead stream. Thus, the feed contains a C2 and lighter components. Similarly for a front-end DC3 configuration, the initial distillation column is the DC3. As the acetylene reactors are on the overhead of this column, the gaseous feed to the reactors is composed of C3 and lighter hydrocarbon. The feed to the front-end selective hydrogenation reactors may be characterized as a clean stream as the high concentration of $H_2$ may suppress green oil formation. Thus, the design does need a spare reactor. The high concentration of $H_2$ may result in the operation being sensitive to initiation of ethylene hydrogenation and this may result in exothermic runaways and poor operational stability due to sensitive to CO fluctuations.

In back-end selective hydrogenation reactor, the acetylene is typically contained in a C2-rich stream whereby stoichiometric amounts of hydrogen, and in some cases small amounts of carbon monoxide, are added to control the extent of acetylene hydrogenation. In this type of application, the reactors may be located at the overhead of the DC2. This hydrogenation configuration may be suitable for moderate acetylene concentrations when the recovery of acetylene is not of interest. Hydrogen may be added in a molar ratio of 1.2 to 2.2 relative to acetylene in the DC2 overhead gas and the mixture may be passed over a fixed bed palladium-based catalyst. The hydrogenated vapor from the reactor system flows through the guard dryer (often referred to as secondary dehydrator) to the ethylene-ethane fractionator (ethylene splitter). The reactor effluent typically contains less than 1 ppm of acetylene but is contaminated with traces of hydrogen and methane which represent the major disadvantage of a back-end acetylene hydrogenation system. The unreacted $H_2$ in the reactor effluent must be removed via a pasteurization section at the top of the ethylene/ethane splitter or via a downstream secondary DC1.

Green Oil, which may be oligomers of acetylene, may cause fairly rapid catalyst deactivation. Therefore, it may be necessary to include spare reactors with facilities for in-situ catalyst regeneration and reduction. Each reactor may be regenerated about 1-4 times a year. Back-end units may have downstream green oil (C6+) removal facilities. Yet this location has the advantage over the front-end hydrogenation in that it allows very accurate control of hydrogen concentration and reaction temperature, which may result in a higher selectivity of the reaction and higher ethylene gain. Green oil polymer may be formed by side reactions of the hydrogenation of acetylene to ethylene and ethane over Pd, Ni, Pt, etc. catalyst. Green oil may occur due the dimerization of acetylene in the presence of hydrogen to butadiene followed by oligomerization with successive addition of acetylene to a chain of molecules adsorbed on the catalyst surface. The amount of green oil formed may decrease as the hydrogen partial pressure increases. The green oil may be a mixture mainly C4 to C20 reactive oligomers of varying composition. The heavier fraction may be adsorbed on the pores catalyst causing eventual loss of the catalyst activity and thus requiring regeneration by steaming out the deposited green oil. The light end components of the green oil remain in the gas phase, part of which may condense into fine droplets with the gas stream leaving the reactor. These fine droplets may cause fouling of the downstream equipment.

Catalyst deactivation by green oil may become a major problem at very low hydrogen to acetylene ratios. Green oil formation may be decreased by the use of silver promoted Pd catalyst on $Al_2O_3$ which help terminate the chain growth at the butadiene stage. Thus, instead of the formation of heavier diolefins oligomers, butadiene exits with the gas. This new catalyst generally reduces the formation of green oil to third or half the amount formed with the non-promoted catalysts. The concentration of the green oil in the gas leaving the hydrogenation reactor is in the order of about 100 ppm to about 1000 ppm dependent upon the operating temperature, age of the catalyst, CO content of the gas, $H_2$/acetylene ratio, etc. The droplet size of green oil condensing in the gas stream downstream of the reactor may be mostly less than 5 micron size. The hydrogenation units may be designed with multi-stage adiabatic reactors with interstage cooling to remove the heat generated by the exothermic hydrogenation reactions of acetylene.

The amount of green oil formed may be primarily function of the concentration of acetylene being converted. Hence, the rate of formation of green oil may be higher from the first bed. Green oil formation may decrease with increasing the partial pressure of $H_2$, which is the main reason for the much lower green oil formed in front-end hydrogenation system as compared to back-end hydrogenation units. Typically in back-end hydrogenation reactors 10-20% of the acetylene is converted to C4 and heavier green oil.

Ethylene plants are expected to operate for a period of 5-7 years between turnarounds. Hence, a spare bed is provided to allow the plant to continue operating, when one of the bed(s) is fouled. The fouled bed is taken out of operation, and the spare bed is placed in service. The green oil is then drained and the fouled bed is regenerated and put on standby mode.

The gas leaving the hydrogenation reactor may be cooled, and more green oil may condense from the vapor phase into fine droplets, which may deposit on downstream heat exchangers, dehydrator beds, and on ethylene fractionator internals. The depositing droplets are polymeric and cause fouling of the equipment thus eventually requiring expensive unplanned shutdowns to clean-up the deposited green oil.

Fuel gas used for the regeneration of the secondary dehydrators may strip out the deposited green oil on the molecular sieves, making the fuel gas contaminated with the green oil. The contaminated gas may cause fouling of the low NOx burner nozzles which may lead to lower furnace efficiency and more frequent and costly burner tip cleaning.

Back-end acetylene hydrogenation system may be characterized by substantial formation of green oil and the need to include green oil removal system to protect the downstream secondary dehydrator and ethylene purification equipment. Different industrial methods may be used for the separation of green oil from the hydrogenation reactor gaseous effluent stream were evaluated including: washing of the wet gas stream from the reactor with a liquid ethylene stream in an absorption tower which may be the most efficient method capable of removing>99.5% of the green oil droplets. Impaction of the wet gas through a packed bed wherein the green oil removal may be sensitive to gas flow rate and distribution through the bed. Alternative impaction separation may be accomplished by a mesh pad in a knockout drum. However, this may be the least efficient removing less than 70% of the green oil droplets.

BRIEF DESCRIPTION OF THE DRAWINGS

These drawings illustrate certain aspects of some of the embodiments of the present invention and should not be used to limit or define the invention.

DETAILED DESCRIPTION

Figure 1:
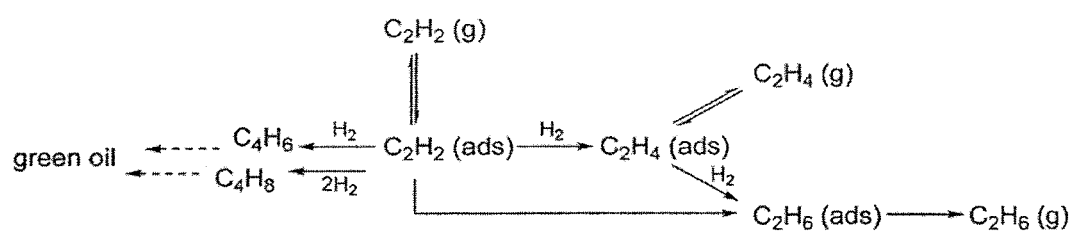
FIG. 1 illustrates an acetylene hydrogenation chemistry map.

In a back-end hydrogenation system, methane, $H_2$ and CO may have been removed in a demethanizer. Therefore, $14_2$ may be added to hydrogenate the acetylene. Under ideal conditions, $H_2$ would be added mol-for-mol to the acetylene with 100% conversion to ethylene. Ideally, this reaction would be unaffected by changes in process conditions, poisons contained in the process gas, or time-on-stream. In practice, a molar excess of $H_2$ may be required because the catalyst is not 100% selective to produce only ethylene and some of the $H_2$ may react further with acetylene to form ethane. Hydrogen may be controllably injected to each bed, for example, at molar $H_2/C_2H_2$ ratios range from about 1.2 to about 2.2. Unreacted $H_2$ in the reactor effluent may be removed via a pasteurization section at the top of the ethylene/ethane splitter or via a downstream secondary demethanizer.

The degree of reaction selectivity may be a function of the $H_2$ partial pressure, the nature of the catalyst, and the reaction temperature. The addition of low levels of CO in concentrations of parts per million to the process stream has been found to moderate and control the hydrogenation process and greatly enhance the selectivity of the catalyst to maximize acetylene conversion to the desired product, ethylene.

When a new or regenerated catalyst bed is placed onstream, conditions of temperature, $H_2/C_2H_2$ ratio, and CO addition may be adjusted to obtain clean-up of acetylene and the maximum selectivity to achieve the largest amount of ethylene gain across the unit. On stream time-on-stream may diminish both the activity and selectivity of the catalyst. This may be due to oligomerization of acetylene and the build-up of heavy oligomeric products such as $C_8$-$C_{20}$ in the pores of the catalyst. Light oligomers such as $C_4$-$C_6$ may remain in the gas phase and be carried to a downstream secondary dehydrator. The heavier oligomers may not have sufficient vapor pressure to stay in a vapor phase and therefore may subsequently condense. The amount of green oil formation may be directly related to the amount of acetylene converted.

Using traditional Pd on $Al_2O_3$ catalysts, the amount of acetylene that dimerizes and becomes polymer forming green oil may be approximately 15-30% of the inlet acetylene. Hence, relatively higher levels of acetylene in a product stream from the steam cracker may produce relatively higher amounts of green oil thereby shortening the cycle time between start-of-run and end-of-run in the back-end hydrogenation system. As green oil is formed and deposited on the catalyst, activity may be regained by increasing operating temperature. However, higher temperatures may decrease selectivity thereby necessitating higher levels of $H_2$. The stepwise process of increasing temperature and $H_2$ may eventually begin to hydrogenate more ethylene to ethane than acetylene. This condition may result in net loss of ethylene across the catalyst bed and eventually catalyst bed regeneration is required. In some embodiments, there may be spare reactors with facilities for in-situ catalyst regeneration and reduction. Each reactor may be regenerated about 1-4 times a year.

A product stream from a stream cracker feeding the acetylene hydrogenation reactor may comprise about 0.5 mol. % to about 2.5 mol. % acetylene, the concentration of acetylene being dependent mainly on the composition of the feedstock to the cracking furnaces as previously described. Most back-end hydrogenation units are configured up to three adiabatic beds operated in series with heat exchange between the beds. One bed at acetylene content below about 5000 ppm, two beds for feed acetylene between about 0.5 mol. % to about 1.7 mol. %, and three beds for feed acetylene between about 1.7 mol. % to about 2.5 mol. %.

Green Oil Droplets may form as a result of condensation from the gas phase ethane-ethylene stream leaving acetylene hydrogenation reactors. Such droplet formation may produce small droplets on the order of about 0.1 µm to about 5 µm with a majority of droplets being less than about 1 µm. A method to remove the green oil droplets may comprise a green oil wash absorber, a green oil static mixer followed by a knock out drum with mesh pad, and/or a green oil knock out drum with mesh pad.

The only effective removal method is using a green oil wash absorber as it is estimated to remove greater than 99.5 mol. % of the green oil in the ethane/ethylene gas stream. The absorber is typically trayed with 10-15 trays and requires the use of large flow rate of purified liquid ethylene stream as absorbing solvent for green oil. The contaminated ethylene solvent is pumped back to the backend deethanizer for its recovery. The ethylene solvent circulation represents 5-10% wt. % of the ethylene product rate, thus using ethylene solvent in this manner reduces the net ethylene production and vastly increases the energy required to operate the ethylene plant. The other disadvantage of this method is that the green oil ends up at the bottom of the backend deethanizer and foul its reboiler and it may travel to the downstream depropanizer and debutanizer fouling their reboilers too.

Another method used for the removal of green oil is to mix the contaminated gas stream with liquid ethylene solvent stream from the ethylene fractionator in a single stage co-current static mixer and then the gas/liquid mixture from the static mixer is separated in a knockout drum. The green oil removal in the single stage co-current static mixer is not as effective as the use of multistage counter-current green oil absorber and has the same disadvantages of reducing the production of ethylene and fouling the deethanizer, depropanizer, and debutanizer reboilers.

A less expensive method for the removal of green oil droplet from the hydrogenated ethylene-ethane stream may be the use of knock out drum with mesh pad consisting of a coarse bed of fiber material. The knock out drum may be configured for a vertical flow and may have a removal efficiency of about 95% wt. % for drops greater than 5 μm. For smaller drops, the removal efficiency may be greatly reduced. The overall green oil separation is in the range of about 70% wt. % to about 80 wt. %. The green oil droplets may flow by gravity to the bottom of the drum where green oil liquid may be intermittently discharged.

Figure 2:
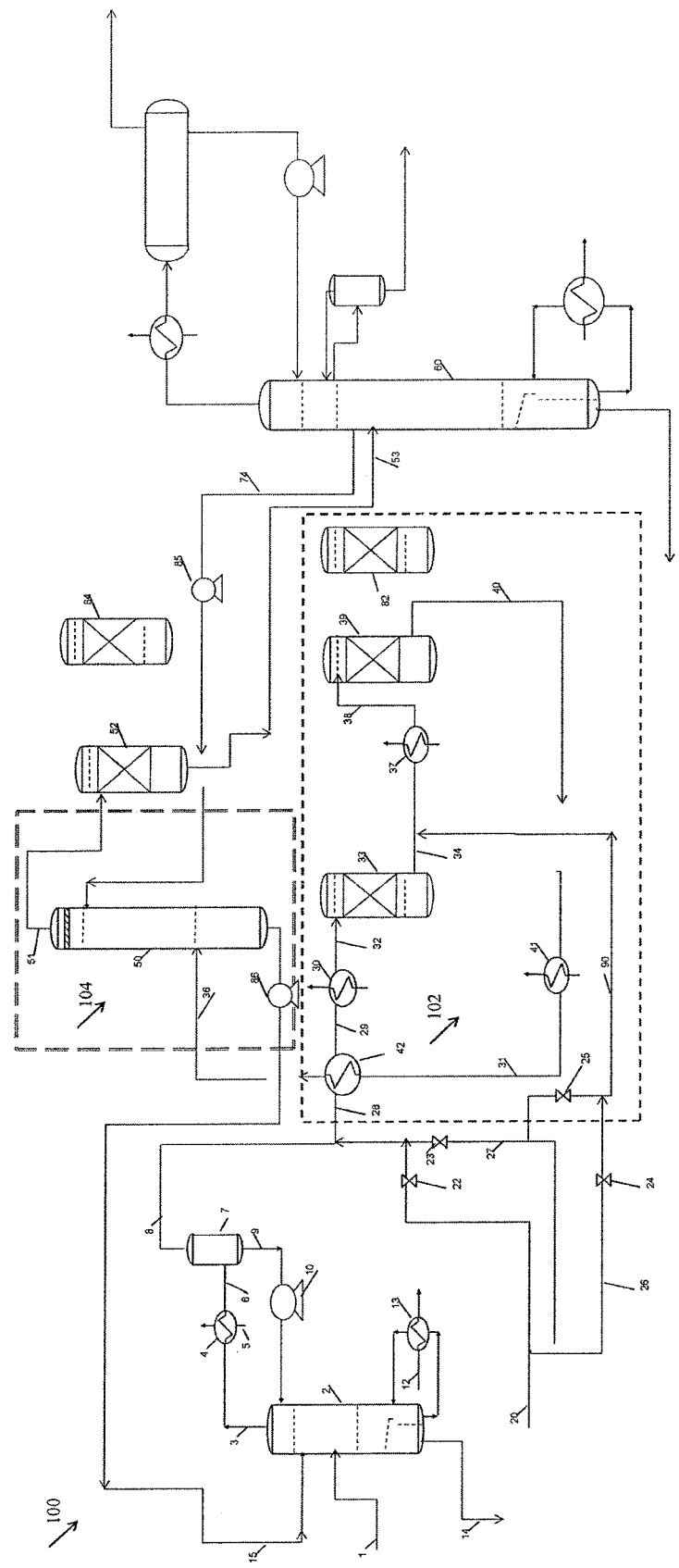
FIG. 2 illustrates a back-end acetylene hydrogenation unit of ethylene plant with a green oil absorber for treating a cooled hydrogenated gas stream.

With reference to FIG. 2, a system 100 for removal of green oil from a treated ethane/ethylene gas stream using an absorber with the acetylene hydrogenation technique is illustrated. System 100 may comprise feed 1 from a bottoms of a demethanizer (not illustrated). Feed 1 may flow to backend deethanizer 2, on flow control. Backend deethanizer 2 may fractionate feed 1 into an overhead C2 stream 3 and a bottoms C3-plus stream 14. The tower overhead may be partially condensed with refrigerant 5 in partial condenser 4. In some embodiments, refrigerant 5 may be propylene. The mixed phase stream 6 from the condenser may flow to backend deethanizer reflux drum 7 which may be a vapor/liquid separator. The liquid reflux 9 may be pumped back to the backend deethanizer 2 via backend deethanizer reflux pump 10 on flow control. The net backend deethanizer overhead vapor 8 from the reflux drum may be fed to the back-end acetylene hydrogenation unit 102. Reboil heat may be provided by hot quench water 12 in the backend deethanizer reboiler 13. Bottom product 14 may be a C3+ stream which may be sent to downstream depropanizer tower (not illustrated). Back-end acetylene hydrogenation unit 102 may comprise first hydrogenation reactor 33 and second hydrogenation reactor 39 and associated process equipment. Back-end acetylene hydrogenation unit 102 may be located downstream of the backend deethanizer 2. The main function of back-end acetylene hydrogenation unit 102 is to hydrogenate C2 acetylene to ethylene and ethane, thereby increasing the overall ethylene production. Hydrogen stream 20 under flow control through valve 22 may be provided to hydrogenate the acetylene component in the net backend deethanizer overhead vapor 8. A previously discussed, carbon monoxide may be added as needed during hydrogenation. Stream 28 may be the feed stream to back-end acetylene hydrogenation unit 102. Stream 28 may be formed by combining hydrogen stream 20, net backend deethanizer overhead vapor 8, and CO stream 27 added as needed under flow control through valve 23. Stream 90 comprising CO and hydrogen under flow control from valve 24 and valve 25 respectively may be mixed with first reactor outlet stream 34.

In some embodiments, stream 28 comprising the backend deethanizer net overhead with added hydrogen and CO may be at pressure of about 22 to about 26 barg (bar gauge) and temperature of about −10° C. to about −15° C. In some embodiments, stream 28 may be heated to a temperature of about 4° C. to 5° C. in cross exchanger 42 using hydrogenated stream 31 to produce stream 29. Hydrogenated stream 31 may be a cooled product from second hydrogenation reactor 39 which may be cooled in cooling water exchanger 41. In some embodiments, stream 29 may further heated in exchanger 30 to a temperature of about 30° C. to about 40° C. to produce stream 32. Stream 32 may be fed to the first hydrogenation reactor 33. The hydrogenation reaction is exothermic which may cause a temperature increase of contents of first hydrogenation reactor 33. Effluent gas 34 from first hydrogenation reactor 33 may be cooled against cooling water in intercooler 37, before flowing into the second hydrogenation reactor 39. Effluent stream 40 from second hydrogenation reactor 39 may be cooled by cooling water in aftercooler 41, and cross exchanger 42 to produce stream 36.

Stream 36 from cross exchanger 42 may flow to a bottoms section of green oil absorber 50 and be counter-currently contacted with ethylene stream 74. Ethylene stream 74 may be from a rectifying section of the ethylene fractionator 60. Ethylene stream 74 may be transferred to green oil absorber 50 by pump 85. Green oil present in stream 36 may be absorbed into ethylene stream 74, hereby removing green oil from the product ethylene. Green oil rich stream 15 comprising ethylene and green oil may be drawn from green oil absorber 50 by pump 89. Green oil rich stream 15 may be pumped to backend deethanizer 2 to recover the ethylene content of green oil rich stream 15 and to fractionate the green oil content of green oil rich stream 15. Green oil may leave backend deethanizer 2 in bottom product 14.

Gas stream 51 from the green oil absorber 50 may flow to the secondary drier 52 to remove any trace quantities of moisture and dried outlet stream 53 may be fed to ethylene fractionator 60. Secondary drier 52 may be regenerated once every few weeks and spare drier 84 may be switched as replacement. Additionally, spare hydrogenation reactor 82 may be provided as in-situ regeneration may be utilized when any of beds of first hydrogenation reactor 33 or second hydrogenation reactor 39 become fouled with green oil. Spare hydrogenation reactor 82 may be piped to first hydrogenation reactor 33 and second hydrogenation reactor 39 to replace capacity when either first hydrogenation reactor 33 or second hydrogenation reactor 39 is being regenerated.

Figure 3:
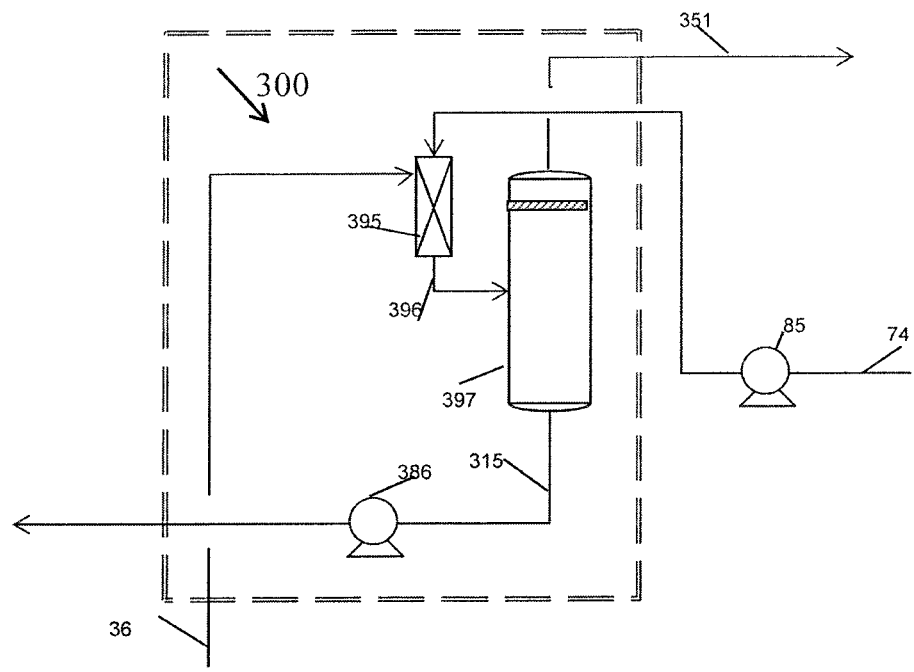
FIG. 3 illustrates green oil removal from cooled hydrogenated gas stream using static mixer followed by knockout drum.

Another technique for removing green oil may comprise using a knockout drum and static mixer. With reference to FIG. 3, green oil removal unit 300 is illustrated. Green oil removal unit 300 may comprise static mixer 395 and knockout drum 397. Stream 36 from back-end acetylene hydrogenation unit 102 may be introduced into static mixer 395 alongside ethylene stream 74. As the streams intermix, green oil droplets from stream 36 may be transferred from stream 36 to ethylene stream 74. Stream 36 may be in a gaseous phase wherein the green oil droplets are entrained within the gas and ethylene stream 74 may be in a liquid phase. Stream 396 exiting static mixer 395 may comprise a mixed gas-liquid phase which may be fed to knockout drum 397. Knockout drum 397 may separate the mixed gas-liquid phase to gas stream 351 and liquid stream 315 wherein liquid stream 315 comprises the portion of green oil absorbed in static mixer 395. The portion of green oil droplets not absorbed by the liquid ethylene in static mixer 395 may be further coalesced to larger droplets as the gas is passed through a mesh pad in the knockout drum resulting in gas stream 351 that may be nearly free of green oil. Gas stream 351 may be sent to ethylene fractionator 60 and liquid stream 315 may be sent to backend deethanizer tower 2 via pump 386 as shown in FIG. 2.

Figure 4:
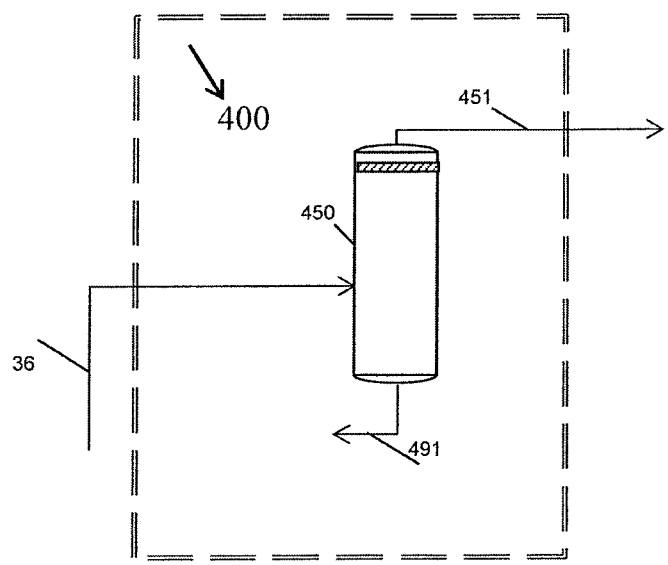
FIG. 4 illustrates green oil removal from cooled hydrogenated gas stream using knockout drum.

Another technique for removing green oil may comprise using a knockout drum. With reference to FIG. 4, green oil removal unit 400 is illustrated. Green oil removal unit 400 may comprise knockout drum 450. Stream 36 from cross exchanger 42, previously illustrated in FIG. 1, may flow to knockout drum 450. Green oil droplets present in stream 36 larger than about 5 μm may coalesce to larger droplets as gasses in stream 36 pass through a mesh pad at the top of knockout drum 450. Larger droplets may become too heavy to remain entrained and may fall down to the bottom of knockout drum 450 by gravity. Cleaned gas stream 451 from knockout drum 450 may flow to secondary drier 52 as illustrated in FIG. 2. Green oil may be collected in the bottom of the knockout drum 450 and may be purged intermittently as stream 491 to a flare.

Each of the previously described techniques for treating green oil may have several drawbacks and design deficiencies. The Green Oil Absorber as shown in FIG. 2 requires significant column size and relatively large recycle flow of purified ethylene which may negatively impact the overall efficiency of the steam cracker and may require a large amount of energy. Additionally, green oil ends up contaminating the bottoms of the backend deethanizer $C3^+$ stream which may foul any equipment downstream of the backend deethanizer. The use of a static mixer to absorb the green oil followed by knockout drum as shown in FIG. 3, may have lower capital costs as a static mixer may be less costly than a tower. However, this method may require even higher recycle flow rates of purified ethylene to cause the same degree of green oil removal, thus, resulting in less efficient process. Separation using a knockout drum comprising a mesh pad for the separation of green oil may have the lowest cost but may offers poor separation performance, especially if droplet sizes are small.

Previous methods of green oil removal may involve specific unit operations downstream of the acetylene hydrogenation system which may suffer performance problems from the presence of fouling species contained within the green oil. The customary sequence of unit operations within a steam cracker for a back-end acetylene hydrogenation configuration are (1) secondary dehydration, then (2) super fractionation of ethylene from ethane then (3) recycle of ethane which exits the bottom of the super fractionator to either (a) the fuel gas mix drum or (b) the steam cracking furnaces whether dedicated to ethane cracking or otherwise co-cracked with a compatible partner such as propane or naphtha. The deleterious effects of retained green oil from the back-end acetylene hydrogenation system for each of the named unit operations are defined below.

Green Oil may be an aerosol contained within the gaseous stream which exits the acetylene hydrogenation unit. The stream must be dried due to the formation of water during the reaction. The equipment for drying the stream may be referred to as secondary dehydrators. In some examples, fixed bed driers using a desiccant or a molecular sieve may be used for water removal. In some examples, there may be multiple secondary dehydrators with, one operating and one spare on standby. The green oil within the gaseous stream to the secondary dehydrators may be adsorbed in the alumina pore structure of the molecular sieve which may prevent proper adsorption of water. As such, the expected cycle time between regeneration of the secondary dehydrator may be sharply reduced leading to much more frequent regenerations of the dehydrator bed(s).

Super fractionation of Ethylene from Ethane: Subsequent to secondary dehydration may follow super fractionation of ethylene from ethane within a typical super fractionator. Without a green oil removal system, there may be carryover of green oil from the secondary dehydrator(s) to the inlet of the super fractionator. Due to its lesser volatility, essentially all green oil from the inlet to the super fractionator may travel to the bottom of the super fractionator with progressive accumulation of green oil polymeric material onto the tray decks and other internals of the super fractionator. This internal accumulation of green oil may foul the tray decks and ultimately prevent liquid and gas from flowing from the tray to the tray such that the capacity profile of the column is largely inhibited from achieving its capacity due to fouling.

Recycle of Ethane to Fuel Gas Mix Drum: Green oil which has not adhered to the column internals of the super fractionator may exit the bottom of the column alongside ethane. The exiting ethane may be sent to the fuel gas system via the fuel gas mix drum. In this case, fuel gas is consumed by either the steam cracking furnaces and/or the offsite steam boilers. In either case, the green oil propensity for fouling the burner tips is high, thereby requiring high maintenance of the burners.

Recycle Ethane to Steam Cracker Feed: Any green oil in the recycle ethane stream fed to the steam cracker feed is highly problematic since those species within the green oil composition profile are hydrogen deficient and represent coking precursors. Green oil may accelerate coke formation in the steam cracking furnace itself.

All of the above symptoms are a consequence of either a poor performing green oil removal system or no green oil removal system at all within the steam cracker.

To overcome the deficiencies of the prior and currently used methods, a method that does not include these drawbacks is disclosed. In particular, it is desired for the system to enable the removal of green oil from the hydrogenated ethane-ethylene stream and eliminate of the use of liquid ethylene solvent and passing the separated green oil to the backend deethanizer tower. The present disclosure relates to the use of a gas/liquid coalescer as an effective means to remove green oil. The coalescer captures small aerosols and combines them into larger, more readily separable drops. In some embodiments, high efficiency gas/liquid coalescers have achieved from about 98 wt. % to about 99 wt. % total green oil removal and in some examples may be rated at 99.99 wt. % removal of drops greater than 0.3 μm. The removal mechanism is based on diffusion or Brownian motion of the aerosol drops in the coalescer media. This mechanism may allow for separation even at lower than design flow rates and a high efficiency gas/liquid coalescers may overcome high turn down ratios. The green oil may collect at the bottom of the gas/liquid coalescer vessel and be intermittently discharged.

The gas/liquid coalescer may be located upstream of the secondary dehydrator to remove green oil before entering the secondary dehydrator. In another embodiment, an additional gas/liquid coalescer is installed downstream of each acetylene hydrogenation reactor to remove the green oil formed in that reactor thereby reducing catalyst fouling in the next reactor and increasing cycle time of the catalyst bed and the overall life of the catalyst.

In an embodiment, a green oil removal system comprising a gas/liquid coalescer may be used to treat a reactor outlet stream. A process utilizing a gas/liquid coalescer may comprise a variety of steps. A first step may comprise preconditioning of the gas stream by using a prefilter to minimize solids and catalyst fines in the coalescer influent that may plug the coalescer, thereby reducing its overall life and efficiency. A second step may comprise coalescence of the entrained green oil droplets using a high efficiency gas/liquid coalescer. The gas/liquid coalescer may merge small droplets of liquid into larger ones as the gas stream passes through several layers of filter media, each with progressively larger pores. As droplets compete for the open pores, they may coalesce forming larger droplets. These larger droplets may be easier to separate from the continuous gas phase. The coalescer size and type may be determined by numerous factors such as, for example, physical properties of the gas and liquid, flow rate, process conditions and chemical compatibility with process fluids and additives. A high efficiency coalescer cartridge may trap droplets down to 0.1 micron. A third step may be separation of the coalesced droplets from the continuous gas phase. The gas/liquid coalescer may be designed such that the velocity of a gas within the gas/liquid coalescer is low enough such that coalesced droplets are do not become entrained in the gas. Separation of the coalesced droplets from the gas may occur when the droplets become sufficient in size to fall out of the gas. High efficiency gas/liquid coalescer units are commercially available from manufacturers such as Pall Filters SepraSol technology, PecoFacet PEACH technology coalescers, and Ultisep Coalescers by Pentair or other equivalent devices.

Figure 5:
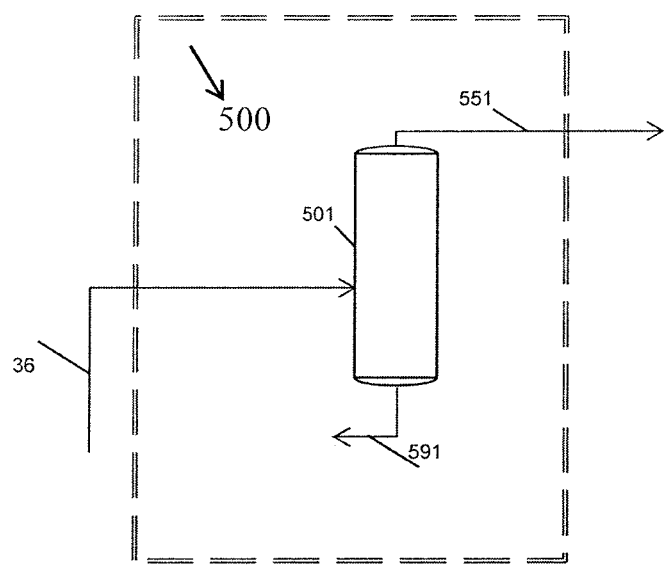
FIG. 5 illustrates green oil removal from cooled hydrogenated gas stream using a gas-liquid coalescer.

With reference to FIG. 5, a green oil removal unit 500 is illustrated. Green oil removal unit 500 may comprise gas/liquid coalescer 501. Stream 36 from exchanger 42, previously illustrated in FIG. 2, may flow to a bottom of the housing into a first stage knock out section in gas-liquid coalescer 501. In the first stage knockout section, any slugs or larger size droplets (approximately 300 μm or greater) may be removed by gravitational settling. The gas may then travel upward through a tube sheet and may flow radially from the inside of the cartridges through the coalescer medium to the annulus. In some embodiments, the inlet green oil aerosol distribution may be in the size range of about 0.1 μm to about 300 μm. After passing through the coalescer medium, in some embodiments, the drops may be transformed to enlarged coalesced droplets in the size range of about 0.5 mm to about 2.2 mm. The formation of the larger coalesced drops may allow their capture onto the fibers of the coalescer media and their eventual draining downward inside the media pack due to the force of gravity, thus freeing the gas from its green oil content. Gas stream 551 from gas-liquid coalescer 501 may flow to the secondary drier 52, as in FIG. 2, to remove any trace quantities of moisture. Separated green oil 591 may collect at the bottom of the coalescer 501, and may be intermittently discharged to a flare.

Figure 6:
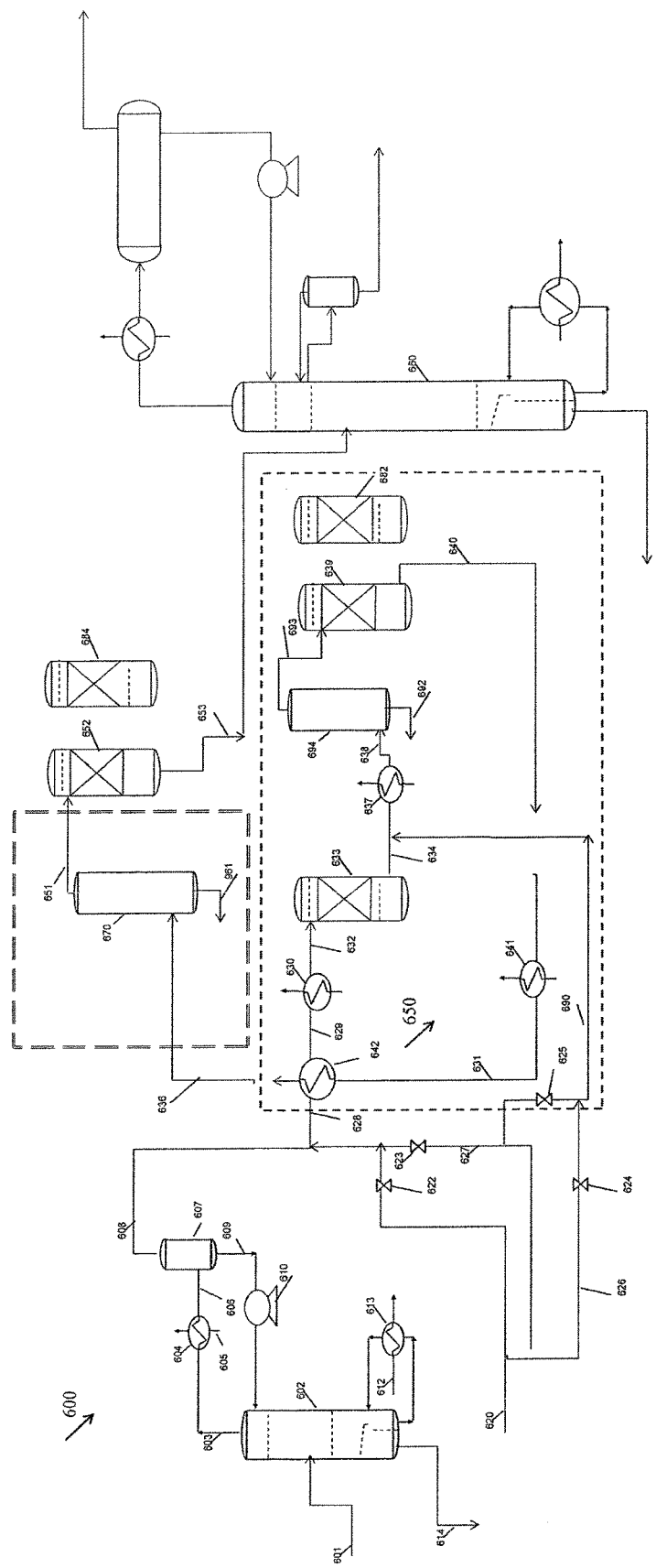
FIG. 6 illustrates green oil removal from cooled gas stream downstream each reactor using a gas-liquid coalescer.

With reference to FIG. 6, another embodiment may comprise removal of green oil using gas/liquid coalescers from the cooled outlet of both reactors in the acetylene hydrogenation unit. The back-end C2 hydrogenation and the downstream ethylene fractionator unit 600 may start with the bottoms from demethanizer stream 601 which may be fed to backend deethanizer 602, on flow control. Backend deethanizer 602 may fractionate the feed into an overhead C2 stream 603 and a bottoms C3-plus stream 614. Backend deethanizer 602 overhead may be partially condensed with a refrigerant 605 in partial condenser 604. Mixed phase stream 606 from partial condenser 604 may flow to a backend deethanizer reflux drum 607 which is a vapor/liquid separator. Liquid reflux 609 may be pumped back to backend deethanizer 602 via the backend deethanizer reflux pump 610 on flow control. Net backend deethanizer overhead vapor 608 from reflux drum 607 may be fed to back-end acetylene hydrogenation unit 650. Reboil heat may be provided by quench water 612 in the backend deethanizer reboiler 613. Bottoms C3-plus stream 614 may feed a downstream depropanizer tower (not illustrated).

Back-end acetylene hydrogenation system 650 may comprise first hydrogenation reactor 633 and second hydrogenation reactor 639 and associated process equipment. Back-end acetylene hydrogenation unit 650 may be located downstream of backend deethanizer 602. The main function of back-end acetylene hydrogenation unit 650 is to hydrogenate C2 acetylene to ethylene and ethane, thereby increasing the overall ethylene production. Hydrogen stream 620 under flow control through valve 622 may be provided to hydrogenate the acetylene component in the net backend deethanizer overhead vapor 608. Stream 626 may be split from hydrogen stream 620 to provide hydrogen to stream 690. A previously discussed, carbon monoxide may be added as needed during hydrogenation. Stream 628 may be the feed stream to back-end acetylene hydrogenation unit 102. Stream 628 may be formed by combining hydrogen stream 620, net backend deethanizer overhead vapor 608, and CO stream 627 added needed as under flow control through valve 623. Stream 690 comprising CO and hydrogen under flow control from valve 624 and valve 625 respectively may be mixed with effluent gas 634.

In some embodiments, stream 628 comprising the back-end deethanizer net overhead with added hydrogen and CO may be at pressure of about 22 to about 26 barg (bar gauge) and temperature of about −10° C. to about −15° C. In some embodiments, stream 628 may be heated to a temperature of about 4° C. to 5° C. in cross exchanger 642 using stream 631 to produce stream 629. Stream 631 may be a cooled product from second hydrogenation reactor 639 which may be cooled in cooling water aftercooler 641. In some embodiments, stream 629 may further heated in exchanger 630 to a temperature of about 30° C. to about 40° C. to produce stream 632. Stream 632 may be fed to the first hydrogenation reactor 633. The hydrogenation reaction is exothermic which may cause a temperature increase of contents of first hydrogenation reactor 633. Effluent gas 634 from first hydrogenation reactor 633 may be cooled against cooling water in intercooler 637, which may cause condensation of green oil present in effluent gas 634. Stream 638 may flow into gas/liquid coalescer 694 where the green oil droplets may further coalesce into larger droplets and separate out collecting in a bottom section of gas/liquid coalescer 694. The collected green oil may intermittently be drawn off as stream 692 and send to a flare. Stream 693 may flow into second acetylene hydrogenation reactor 639. Effluent stream 640 from second hydrogenation reactor 639 may be cooled by cooling water in aftercooler 641, and cross exchanger 642 to produce stream 636.

Stream 636 from cross exchanger 642 may flow to the gas/liquid coalescer 670. Stream 636 may comprise liquid green oil aerosol contamination. Stream 636 may enter at the bottom of gas/liquid coalescer 670 into a first stage knock out section. Here any slugs or larger size droplets (approximately greater than 300 μm) of green oil may be removed by gravitational settling. The gas may travel upward through a tube sheet and may flow radially from the inside of the cartridges through the coalescer medium to the annulus. In some embodiments, the inlet green oil aerosol distribution may be in the size range of about 0.1 μm to about 300 μm. After passing through the coalescer medium, in some embodiments, the droplets may be transformed to enlarged coalesced droplets in the size range of about 0.5 mm to about 2.2 mm. The formation of the large coalesced drops may allow their capture onto the fibers of the coalescer medium and thereafter be drained downward inside the media pack due to the force of gravity, thus freeing the gas from its green oil content. Steam 961 comprising the coalesced green oil may be periodically drawn off and sent to flare. Stream 651 may have nearly all green oil and acetylene removed as compared to steam 636. In some embodiments, stream 651 may comprise less than about 1 ppm acetylene and less than about 1 ppm green oil. Alternatively, stream 651 may comprise less than 0.1 ppm acetylene and 0.1 ppm green oil. Still further, stream 651 may comprise 0 ppm acetylene and 0 ppm green oil.

Stream 651 from gas/liquid coalescer 670 may flow to secondary drier 652 to remove any trace quantities of moisture. Dried outlet stream 653 may feed to ethylene fractionator 660. Ethylene fractionator 660 may produce an overhead stream comprising the ethylene from dried outlet stream 653. The drier may be regenerated once every few weeks and the spare drier, 684, may be switched as replacement. Additionally, spare hydrogenation reactor 682 may be provided as in-situ regeneration may be utilized when any of beds of first hydrogenation reactor 633 or second hydrogenation reactor 639 become fouled with green oil. Spare hydrogenation reactor 682 may be piped to first hydrogenation reactor 633 and second hydrogenation reactor 639 to replace capacity when either first hydrogenation reactor 633 or second hydrogenation reactor 639 is being regenerated.

EXAMPLES

Simulations were run for a back-end acetylene hydrogenation reactor using two different feedstocks to a steam cracker. The feedstocks were mixed ethane/propane and naphtha. The catalyst used in each simulation is silver promoted palladium. The hydrogenation reaction in each bed is controlled such that nearly equal temperature rise occurred across each bed.

Example 1

The first simulation was performed with mixed ethane and propane feedstock to a gas cracker with a silver promoted palladium catalyst in the hydrogenation reactors. The temperature ranges for the two reactor beds are displayed in Table 2. The results of the simulation are displayed in Table 3.

TABLE 2

| | | | Temperature ° C. | | | |
|---|---|---|---|---|---|---|
| 1st Bed | SOR Inlet | 32° C. | SOR Outlet | 44° C. | $\Delta T_{SOR}$ | 12° C. |
| 1st Bed | EOR Inlet | 77° C. | EOR Outlet | 96° C. | $\Delta T_{EOR}$ | 19° C. |
| 2nd Bed | SOR Inlet | 41° C. | SOR Outlet | 55° C. | $\Delta T_{SOR}$ | 14° C. |
| 2nd Bed | EOR Inlet | 85° C. | EOR Outlet | 103° C. | $\Delta T_{EOR}$ | 18° C. |

SOR = Start Of Run
EOR = End Of Run

It was observed that gas/liquid coalescer 694 and gas/liquid coalescer 670 were effective at reducing green oil content of the effluent of first hydrogenation reactor 633 and effluent of second hydrogenation reactor 639. Stream 638 is an outlet stream from intercooler 637 feeding into gas/liquid coalescer 694, and stream 693 is an outlet from gas/liquid coalescer 694. Green oil content in stream 638 and stream 693 was observed to be 0.4 kmol/hr and 0.0 kmol/hr respectively. Stream 636 is an outlet from cross exchanger 642 and stream 651 is an outlet from gas/liquid coalescer 670. Green oil content in streams 636 and 651 was observed to be 0.12 kg/hr and 0.00 kg/hr respectively.

TABLE 3

| | | Stream | | | | | |
|---|---|---|---|---|---|---|---|
| Composition, kgmol/hr | MW | 601 DC2 Feed | 614 DC2 BTMS | 608 DC2 OVHD | 632 FD to 1St STG | 634 1St STG OUTLET | 1* | 693 2ND STG INLET |
| Hydrogen | 2.02 | 0.00 | 0.00 | 0.00 | 25.50 | 2.50 | | 12.80 |
| Carbon Monoxide | 28.01 | 0.00 | 0.00 | 0.00 | 0.00 | 0.00 | | 0.00 |
| Methane | 16.04 | 0.57 | 0.00 | 0.57 | 0.57 | 2.21 | | 2.21 |
| Acetylene | 26.04 | 30.88 | 0.00 | 30.88 | 30.88 | 12.35 | | 12.35 |
| Ethylene | 28.05 | 3436.95 | 0.00 | 3436.95 | 3436.95 | 445.11 | | 3445.11 |
| Ethane | 30.07 | 1714.12 | 0.05 | 1714.06 | 1714.06 | 1721.19 | | 1721.19 |
| MAPD | 40.06 | 7.84 | 7.84 | 0.00 | 0.00 | 0.00 | | 0.00 |
| Propylene | 42.08 | 279.81 | 272.09 | 7.73 | 7.73 | 7.73 | | 7.73 |
| Propane | 44.1 | 119.31 | 118.73 | 0.58 | 0.58 | 0.58 | | 0.58 |
| C4's | 54.09 | 89.26 | 89.26 | 0.00 | 0.00 | 0.80 | | 0.80 |
| C5's | | 28.29 | 28.29 | 0.00 | 0.00 | | | |
| Benzene | 78.12 | 16.42 | 16.42 | 0.00 | 0.00 | 0.00 | | 0.00 |

TABLE 3-continued

| | | | | | | | | |
|---|---|---|---|---|---|---|---|---|
| Fuel Oil | | 1.76 | 1.76 | 0.00 | 0.00 | | | 0.00 |
| C6-C8 | | 0.00 | 0.00 | 0.00 | 0.00 | 0.40 | 0.40 | 0.00 |
| C10-C18 | | 0.00 | 0.00 | 0.00 | 0.00 | 0.70 | 0.70 | 0.00 |
| Total Molar Flowrate | kmol/hr | 5725.21 | 534.44 | 5190.77 | 5216.27 | 5193.57 | | 5202.77 |
| Total Mass Flowrate | kg/hr | 17492.18 | 25265.81 | 14126.37 | 149142.25 | 149214.82 | | 149214.82 |
| Total Molecular Weight | | 30.46 | 47.28 | 28.73 | 28.59 | 28.73 | | 28.68 |
| Temperature | °C. | −5.00 | 77.78 | −10.56 | 76.67 | 96.11 | | 85.00 |
| Pressure | barg | 24.97 | 25.17 | 24.48 | 21.72 | 21.72 | | 21.70 |

| | | | | Stream | | | |
|---|---|---|---|---|---|---|---|
| Composition, kgmol/hr | | MW | 640 2ND STG OUTLET | 2* | 651 GO G/L COALESR OUTLET | 620 H2 FEED | 653 FD TO C2 SPLITTER |
| | Hydrogen | 2.02 | 1.56 | | 1.56 | 51.76 | 1.56 |
| | Carbon Monoxide | 28.01 | 0.00 | | 0.00 | 0.00 | 0.00 |
| | Methane | 16.04 | 3.30 | | 3.30 | 2.73 | 3.30 |
| | Acetylene | 26.04 | 0.00 | | 0.00 | 0.00 | 0.00 |
| | Ethylene | 28.05 | 3449.20 | | 3447.76 | 0.00 | 3447.70 |
| | Ethane | 30.07 | 1724.76 | | 1724.76 | 0.00 | 1724.76 |
| | MAPD | 40.06 | 0.00 | | 0.00 | 0.00 | 0.00 |
| | Propylene | 42.08 | 7.73 | | 7.73 | 0.00 | 7.73 |
| | Propane | 44.1 | 0.58 | | 0.58 | 0.00 | 0.58 |
| | C4's | 54.09 | 1.00 | | 1.00 | 0.00 | 1.00 |
| | C5's | | 0.03 | | 0.03 | 0.00 | 0.03 |
| | Benzene | 78.12 | 0.00 | | 0.00 | 0.00 | 0.00 |
| | Fuel Oil | | | | | 0.00 | 0.00 |
| | C6-C8 | | 0.12 | 0.12 | 0.00 | 0.00 | 0.00 |
| | C10-C18 | | 0.21 | 0.21 | 0.00 | 0.00 | 0.00 |
| | Total Molar Flowrate | kmol/hr | 5188.48 | | 5186.71 | 54.48 | 5186.65 |
| | Total Mass Flowrate | kg/hr | 149273.79 | | 149273.79 | 148.33 | 149247.94 |
| | Total Molecular Weight | | 28.77 | | 28.78 | 2.72 | 28.78 |
| | Temperature | °C. | 98.33 | | 1.11 | 10.00 | 10.00 |
| | Pressure | barg | 20.69 | | 20.34 | 43.38 | 19.00 |

1* - C6-C8 components formed on cooling the first stage outlet gas are removed by gal/liquid coalescer. C10-C18 components formed in the first stage bed are deposited on the catalyst in the first stage bed.
2* - C6-C8 components formed on cooling the second stage outlet gas are removed by gal/liquid coalescer. C10-C18 components formed in the second stage bed are deposited on the catalyst in the second stage bed.

Example 2

A second simulation was performed with naphtha feedstock to a gas cracker with a silver promoted palladium catalyst in the hydrogenation reactors. The temperature ranges in for the two reactor beds are displayed in Table 4. The results of the simulation are displayed in Table 5.

TABLE 4

| | | | Temperature °C. | | | |
|---|---|---|---|---|---|---|
| 1st Bed | SOR Inlet | 40 | SOR Outlet | 74 | $\Delta T_{SOR}$ | 34 |
| | EOR Inlet | 84 | EOR Outlet | 129 | $\Delta T_{EOR}$ | 45 |

TABLE 4-continued

| | | | Temperature °C. | | | |
|---|---|---|---|---|---|---|
| 2nd Bed | SOR Inlet | 43 | SOR Outlet | 75 | $\Delta T_{SOR}$ | 32 |
| | EOR Inlet | 89 | EOR Outlet | 138 | $\Delta T_{EOR}$ | 49 |

SOR = Start Of Run
EOR = End Of Run

It was observed that gas/liquid coalescer 694 and gas/liquid coalescer 670 were effective at reducing green oil content of the effluent of first hydrogenation reactor 633 and effluent of second hydrogenation reactor 639. Stream 638 is an outlet stream from intercooler 637 feeding into gas/liquid coalescer 694, and stream 693 is an outlet from gas/liquid coalescer 694. Green oil content in stream 638 and stream 693 was observed to be 0.4 kmol/hr and 0.0 kmol/hr respectively. Stream 636 is an outlet from cross exchanger 642 and stream 651 is an outlet from gas/liquid coalescer 670. Green oil content in streams 636 and 651 was observed to be 0.12 kg/hr and 0.00 kg/hr respectively.

TABLE 5

| Composition, kgmol/hr | MW | 601 DC2 Feed | 614 DC2 BTMS | 608 DC2 OVHD | 632 FD to 1St STG | 634 1St STG OUTLET | 1* | 693 2ND STG INLET |
|---|---|---|---|---|---|---|---|---|
| Hydrogen | 2.02 | 0.0 | | 0.0 | 71.6 | 10.00 | | 36.90 |
| Carbon Monoxide | 28.01 | 0.0 | | 0.0 | 0.0 | 0.00 | | 0.00 |
| Methane | 16.04 | 0.2 | | 0.0 | 0.0 | 4.00 | | 4.00 |
| Acetylene | 26.04 | 86.8 | | 86.8 | 86.8 | 29.50 | | 29.50 |
| Ethylene | 28.05 | 4754.2 | | 4754.2 | 4754.2 | 4777.09 | | 4777.09 |
| Ethane | 30.07 | 953.1 | 0.5 | 953.1 | 953.1 | 973.12 | | 973.12 |
| MAPD | 40.06 | 8.0 | 8.0 | 0.0 | 0.0 | 0.00 | | 0.00 |
| Propylene | 42.08 | 940.1 | 935.3 | 4.8 | 4.8 | 4.80 | | 4.80 |
| Propane | 44.1 | 24.3 | 24.3 | | | | | |
| C4's | 54.09 | 6.3 | 0.9 | 0.0 | 0.0 | 1.43 | | 1.43 |
| C5's | | 0.00 | | 0.0 | 0.0 | 0.00 | | 0.00 |
| Benzene | 78.12 | 0.00 | | | 0.0 | 0.00 | | 0.00 |
| Fuel Oil | | | | | 0.0 | | | |
| C6-C8 | | | | | 0.0 | 0.40 | 0.40 | 0.00 |
| C10-C18 | | | | | 0.0 | 1.78 | 1.78 | 0.00 |
| Total Molar Flowrate | kmol/hr | 6772.96 | 968.99 | 5798.87 | 5870.47 | 5802.13 | | 5826.85 |
| Total Mass Flowrate | kg/hr | 205588.54 | 40814.23 | 164495.64 | 164755.50 | 164880.55 | | 164501.99 |
| Total Molecular Weight | | 30.35 | 42.12 | 28.37 | 28.07 | 28.42 | | 28.23 |
| Temperature | °C. | 10.00 | 38.90 | −15.70 | 76.67 | 96.11 | | 85.00 |
| Pressure | barg | 29.40 | 26.00 | 25.20 | 21.72 | 21.72 | | 21.80 |

| Composition, kgmol/hr | MW | 640 2ND STG OUTLET | 2* | 651 GO G/L COALESR OUTLET | 620 H2 FEED | 653 FD TO C2 SPLITTER |
|---|---|---|---|---|---|---|
| Hydrogen | 2.02 | 4.00 | | 4.00 | 98.5 | 4.00 |
| Carbon Monoxide | 28.01 | 0.00 | | 0.00 | 0.00 | 0.00 |
| Methane | 16.04 | 5.30 | | 5.30 | 7.32 | 5.30 |
| Acetylene | 26.04 | 0.00 | | 0.00 | 0.00 | 0.00 |
| Ethylene | 28.05 | 4788.89 | | 4788.89 | 0.00 | 4788.89 |
| Ethane | 30.07 | 983.42 | | 983.42 | 0.00 | 983.42 |
| MAPD | 40.06 | 0.00 | | 0.00 | 0.00 | 0.00 |
| Propylene | 42.08 | 4.80 | | 4.80 | 0.00 | 4.80 |
| Propane | 44.1 | | | | 0.00 | |
| C4's | 54.09 | 2.17 | | 2.17 | 0.00 | 2.17 |
| C5's | | 0.03 | | 0.03 | 0.00 | |
| Benzene | 78.12 | 0.00 | | 0.00 | 0.00 | 0.00 |
| Fuel Oil | | | | | 0.00 | 0.00 |
| C6-C8 | | 0.12 | 0.12 | 0.00 | 0.00 | 0.00 |
| C10-C18 | | 0.93 | 0.93 | 0.00 | 0.00 | 0.00 |
| Total Molar Flowrate | kmol/hr | 5789.66 | | 5788.61 | 105.82 | 5788.59 |
| Total Mass Flowrate | kg/hr | 164494.54 | | 164281.74 | 397.40 | 164734.20 |
| Total Molecular Weight | | 28.41 | | 28.38 | 3.76 | 28.46 |
| Temperature | °C. | 98.33 | | 1.11 | 10.00 | 10.00 |
| Pressure | barg | 20.69 | | 20.34 | 43.38 | 19.00 |

1* - C6-C8 components formed on cooling the first stage outlet gas are removed by gal/liquid coalescer. C10-C18 components formed in the first stage bed are deposited on the catalyst in the first stage bed.
2* - C6-C8 components formed on cooling the second stage outlet gas are removed by gal/liquid coalescer. C10-C18 components formed in the second stage bed are deposited on the catalyst in the second stage bed.

The concentration of green oil in the feed to the second hydrogenation reactor cooled to about 40° C. at SOR and 85° C. at EOR wherein the product contained 100 to 250 ppm green oil for the case of ethylene and propylene feedstock cracking and 130 to 400 ppm green oil for the case of naphtha feedstock cracking. Green oil in the cooled feed to the second hydrogenation reactor may be carried with the process gas stream in the form of condensed fine liquid droplets of approximately 0.1-300 microns. The liquid droplets may deposit and become adsorbed on the catalyst of the second hydrogenation reactor and eventually further react to higher molecular oligomers and thus increase fouling of the second hydrogenation reactor. To improve the acetylene hydrogenation operation and reduce fouling of the second hydrogenation reactor, a green oil removal system on the cooled feed to the second hydrogenation reactor bed may be provided. The green oil removal system may comprise a knock out drum, green oil absorber, or a gas-liquid coalescer. The use of a gas/liquid coalescer, as illustrated by the examples, may be a preferred choice since as gas/liquid coalescer may remove essentially all the green oil droplets at a relatively low cost. Removal of green oil from the feed to the second hydrogenation reactor reduced oligomer formation on the catalyst. The above examples confirm that green oil, as produced within a back-end acetylene hydrogenation reactor configuration, may be effectively removed from each reactor outlet. The formation of green oil (C6-C8 components) may be a function of multiple variables, reactor inlet/outlet temperature, SOR and EOR conditions, catalyst formulation, and residence time as a function of space velocity, among other factors.

Therefore, the present embodiments are well adapted to attain the ends and advantages mentioned as well as those that are inherent therein. The particular embodiments disclosed above are illustrative only, as the present embodiments may be modified and practiced in different but equivalent manners apparent to those skilled in the art having the benefit of the teachings herein. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method to reduce green oil in an ethylene cracking plant, the method comprising:
   cracking a hydrocarbon feedstock in a steam cracker to produce a cracked gas effluent;
   thereafter, performing the following steps in sequential order:
      1. quenching the cracked gas effluent;
      2. compressing the cracked gas effluent;
      3. caustic treating the cracked gas effluent; and
      4. fractionating the cracked gas effluent in a demethanizer to produce a bottoms stream comprising ethylene, ethane, acetylene, and C3+;
   fractionating the bottoms stream in a backend deethanizer to produce a backend deethanizer overhead stream comprising ethylene, ethane, and acetylene;
   feeding the backend deethanizer overhead stream to a first acetylene hydrogenation reactor;
   hydrogenating at least a portion of the acetylene in the backend deethanizer overhead stream in the first acetylene hydrogenation reactor to produce a first reactor effluent stream comprising ethylene, ethane, acetylene, and green oil;
   feeding the first reactor effluent stream to a first gas/liquid coalescer;
   removing at least a portion of the green oil from the first reactor effluent stream to produce a first cleaned effluent stream comprising ethylene, ethane, acetylene, and green oil in an amount less than the green oil present in the first reactor effluent stream;
   feeding the first cleaned effluent stream to a second acetylene hydrogenation reactor;
   hydrogenating at least a portion of the acetylene in the first cleaned effluent stream in the second acetylene hydrogenation reactor to produce a second reactor effluent stream comprising ethylene, ethane, acetylene, and green oil;
   feeding the second reactor effluent stream, to a second gas/liquid coalescer; and
   removing at least a portion of the green oil from the second reactor effluent stream to produce a second cleaned effluent stream comprising ethylene, ethane, acetylene, and green oil in an amount less than the green oil present in the second reactor effluent stream.

2. The method of claim 1, further comprising:
   combining the backend deethanizer overhead stream with hydrogen, carbon monoxide, or both the hydrogen and the carbon monoxide prior to the step of feeding the backend deethanizer overhead stream to a first acetylene hydrogenation reactor.

3. The method of claim 1, wherein the second cleaned effluent stream comprises less than 0.1 ppm green oil.

4. The method of claim 1, further comprising:
   feeding the second cleaned effluent stream to a drier.

5. The method of claim 1 further composing:
   feeding the second cleaned effluent to an ethylene fractionator; and
   producing an overhead ethylene stream.

6. A method comprising:
   feeding a backend deethanizer overhead stream comprising ethylene, ethane, and acetylene to a hydrogenation reactor;
   hydrogenating at least a portion of the acetylene in the backend deethanizer overhead stream to form a first reactor effluent stream comprising ethylene, ethane, acetylene, and green oil;
   feeding the first reactor effluent stream to a first gas/liquid coalescer and removing at least a portion of the green oil from the first reactor effluent stream to produce a first clean effluent stream comprising ethylene, ethane, and acetylene;
   feeding the first clean effluent stream to a second acetylene hydrogenation reactor;
   hydrogenating at least a portion of the acetylene in the first cleaned effluent stream in the second acetylene hydrogenation reactor to produce a second reactor effluent stream comprising ethylene, ethane, acetylene, and green oil; and
   feeding the second reactor effluent stream, to a second gas/liquid coalescer and removing at least a portion of the green oil from the second reactor effluent stream.

7. The method of claim 6, further comprising:
   fractionating a demethanizer bottoms stream in a backend deethanizer to produce the backend deethanizer overhead stream prior to the step of feeding the backend deethanizer overhead stream to the hydrogenation reactor.

8. The method of claim 6, further comprising:
   combining the backend deethanizer overhead stream with hydrogen, carbon monoxide, or a combination of hydrogen and carbon monoxide before the step of feeding the backend deethanizer overhead stream comprising ethylene, ethane, and acetylene to the hydrogenation reactor.

9. The method of claim 6, further comprising:
cooling the first reactor effluent stream prior to the step of feeding the reactor effluent stream to the first gas/liquid coalescer, wherein the cooling causes at least a portion of the green oil in the reactor effluent stream to condense to form a green oil aerosol.

10. The method of claim 6, wherein the first gas/liquid coalescer removes the at least a portion of the green oil by coalescing the green oil aerosol.

11. The method of claim 6, wherein about 98% wt. % or more of the green oil is removed from the first reactor effluent stream.

12. The method of claim 6, wherein the first gas/liquid coalescer comprises a prefilter, filter media comprising pores, and a means to separate coalesced green oil droplets.

\* \* \* \* \*